United States Patent [19]
Leblond et al.

[11] Patent Number: 6,098,423
[45] Date of Patent: Aug. 8, 2000

[54] METHOD OF PREPARING $H_2S$ FOR AN ISOTOPIC ANALYSIS

[75] Inventors: Claudette Leblond, La Celle Saint Cloud; Alain Prinzhofer, rue Fabre d'Eglantines, both of France

[73] Assignee: Institute Francais du Petrole, Cedex, France

[21] Appl. No.: 09/154,863

[22] Filed: Sep. 16, 1998

[30] Foreign Application Priority Data

Sep. 18, 1997 [FR] France ..................... 97 11736

[51] Int. Cl.[7] ............... F25J 3/00; G01N 33/24
[52] U.S. Cl. ................... 62/618; 62/633; 436/32; 436/121
[58] Field of Search ............... 62/62, 600, 633, 62/617, 618; 250/282, 288; 436/25, 32, 121

[56] References Cited

U.S. PATENT DOCUMENTS

| | | | |
|---|---|---|---|
| 4,659,675 | 4/1987 | Demaison et al. | 436/29 |
| 4,866,270 | 9/1989 | Hall et al. | 250/282 |
| 4,988,494 | 1/1991 | Lagas et al. | |

FOREIGN PATENT DOCUMENTS

| 2298106 | of 1976 | France . |
|---|---|---|
| 2420754 | of 1979 | France . |

*Primary Examiner*—William Doerrler
*Attorney, Agent, or Firm*—Antonelli, Terry, Stout & Kraus, LLP

[57] ABSTRACT

A method which enables the sulphur and/or hydrogen contained in a low quantity in hydrogen sulphide to be prepared:

1) the $H_2S$ is oxidized at a temperature and for a duration selected to obtain full oxidation of the $H_2S$ into $SO_2$ and at least two products are obtained at the end of this step: $SO_2$ and $H_2O$,
2) The two products $SO_2$ and $H_2O$ obtained at the end of step 1) are separated,
3) the isotope of the sulphur contained in the sulphur dioxide obtained during step 2) is measured and/or
4) the $H_2O$ obtained during step 2) is brought into contact with an agent capable of reducing the water to hydrogen form and
5) the isotope of the hydrogen is measured.

9 Claims, 7 Drawing Sheets

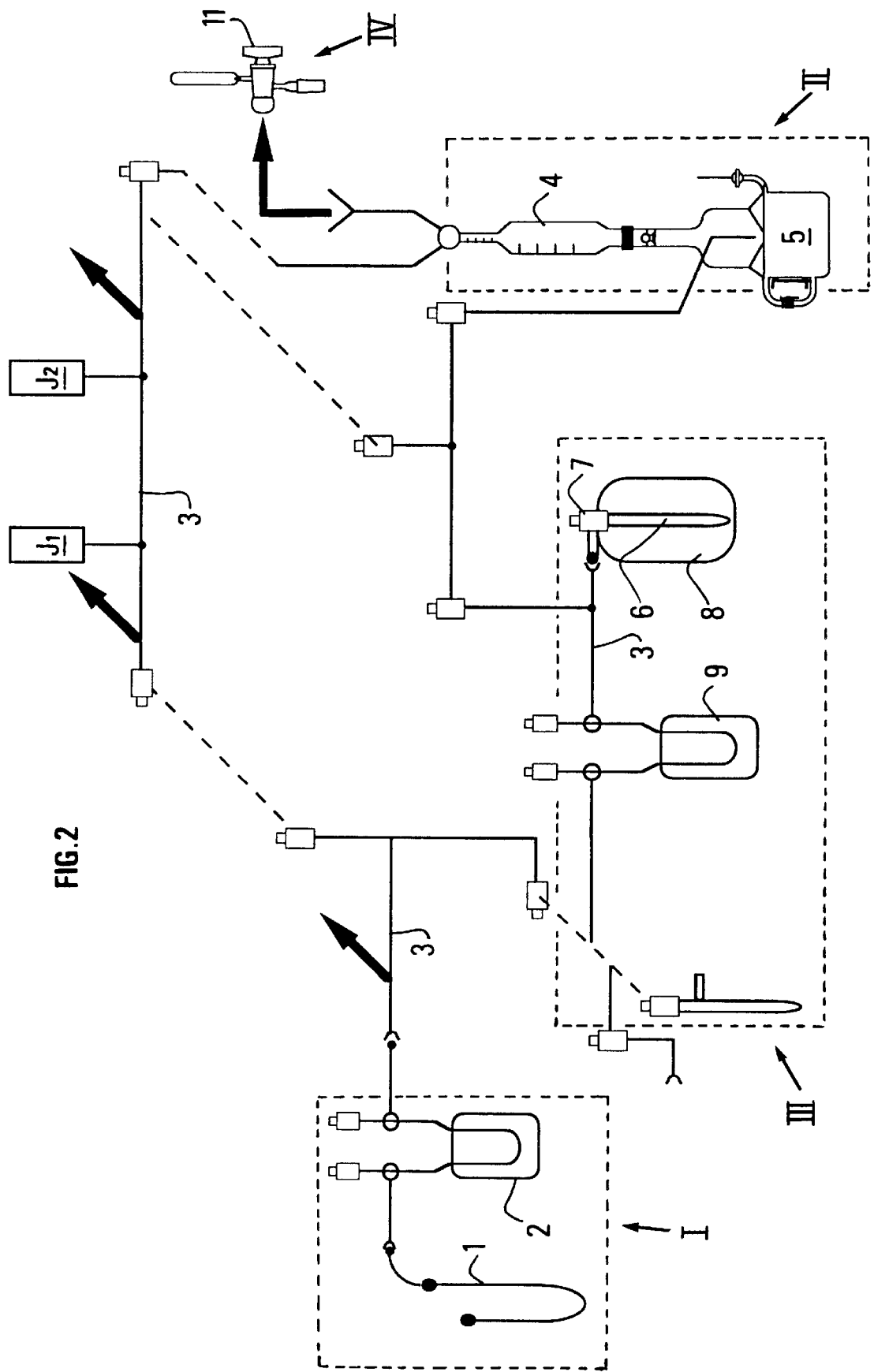

-196°C  22°C

-105°C

METHOD OF PREPARING H₂S FOR AN ISOTOPIC ANALYSIS

The method of the invention enables hydrogen sulphide and in particular sulphur and hydrogen to be prepared in readiness for taking isotopic measurements on these two elements.

The presence or absence of $H_2S$ in natural gas deposits appears to be one of the crucial factors in assessing the risks inherent in petroleum and gas exploration. In order to minimise these risks, it is important to characterise the possible sources of this gas accurately. These sources are generally bacterial, thermogenic (cracking of kerogen or a sulphurous oil) or organo-mineral, for example thermoreduction of sulphates by the hydrocarbons.

FIG. 1A illustrates the steps incorporated in an analysis method used in the prior art. $H_2S$ is bubbled in a solution of cadmium acetate to produce a quantitative precipitation of the sulphur based on the reaction $(CH_3COO)_2Cd + H_2S \rightarrow CdS + 2CH_3COOH$. This step takes place in an aqueous medium. The cadmium sulphice (CdS) precipitate obtained is then isolated by centrifugation, for example, washed until its pH is neutral and then dried in an oven. This is followed by a combustion step which converts the sulphur to a form of $SO_2$, on which the isotopic measurement is then taken. Although this method is relatively easy to implement, it does have the following disadvantages:

being conducted in an aqueous medium, it is necessary to provide a sufficient quantity of $H_2S$ to produce efficient bubbling, it uses a toxic heavy metal (cadmium).

In addition, it does not provide a means of taking an isotopic measurement of hydrogen which would advantageously give additional information about the source of the $H_2S$.

The method of the invention overcomes these disadvantages of the prior art.

It consists in preparing or conditioning the sulphur and/or hydrogen using compounds containing low quantities of hydrogen sulphide, $H_2S$, with a view to conducting isotopic measurements on these two constituents, for example.

The present invention relates to a method of preparing the sulphur and/or hydrogen contained in the hydrogen sulphide $H_2S$ present in a gas or a compound in a small quantity.

The method is characterised in that it comprises the following steps:

1) the $H_2S$ is oxidised at a temperature and for a duration selected so as to bring about total oxidation of the $H_2S$ into $SO_2$ and obtain at least two products, $SO_2$ and $H_2O$ at the end of this step,
2) the two products $SO_2$ and $H_2O$ obtained at the end of step 1) are separated,
3) the isotopic measurement is taken on the sulphur contained in the sulphur dioxide obtained in step 2) and/or
4) the $H_2S$ obtained in step 2) is brought into contact with an agent capable of reducing it to hydrogen form and
5) the isotopic measurement is taken on the hydrogen.

By virtue of one implementing method, the products or elements $SO_2$, $H_2$ and $H_2S$ can be transferred under conditions substantially close to cryogenic conditions.

The step during which the products are separated, step 2), is conducted at a temperature close to −100° C., for example, in order to release the sulphur dioxide and then at a temperature in the order of 90° C. in order to give off the water.

Activated zinc can be used as the agent for reducing the water in step 4).

The hydrogen produced in step 4) is separated under conditions essentially close to cryogenic conditions, for example, in order to trap any impurities.

Steps 1) to 3) at least can be conducted using a compound containing hydrogen sulphide in a small quantity, for example, less than 50 μmoles and preferably between 5 and 50 μmoles.

The method is particularly well suited to measuring the isotope of the sulphur and/or hydrogen making up the hydrogen sulphide present in a natural gas.

The method of the invention has the following specific advantages compared with the prior art:

it can be applied to compounds containing a small quantity of hydrogen sulphide, it makes the hydrogen available for isotopic measurement, it can be applied as a means of following the physical and chemical evolution of the hydrogen sulphide, it does not require the use of toxic compounds.

Other features and advantages of the invention will become clearer from the following description, given by way of example and not restrictive in any respect, and with reference to the appended drawings, in which:

FIGS. 1A and 1B illustrate in diagrammatic form the steps of the bubbling method of the prior art and those of the invention, FIG. 2 is a diagram of one example of how the various devices used to perform the different steps of the method are set up, FIGS. 3A to 3H illustrate the sequence of different steps to be carried out, FIGS. 4 and 5 illustrate the isotopic measurement curves for the sulphur and hydrogen from samples of different origins.

The description given below does not specify details of the sampling devices, storage and measuring devices or pumping means used to implement the method since those specialised in analysis will generally be familiar with these devices. The devices can be set up in a complete analysis circuit or may be used individually and connected to one another in order to run the steps of the method described below.

FIG. 2 shows a vacuumn line 3 on which the various devices are linked.

As an illustration of the method but not restrictively, the gas used may contain the following constituents.

$H_2$, $CH_4$, CO, $N_2$ which are the non-condensible constituents and $CO_2$, $C_2$, $H_2S$, $C_3$, $C_4$ and $C_5$ which are the condensible constituents, in proportions which may vary The quantity of hydrogen sulphide is low, being less than 50 μmoles.

FIG. 3 illustrates a unit comprising means arranged around the vacuum line 3 enabling the method and its complementary steps to be implemented, broken down in the diagram into four parts I, II, III and IV, used solely to provide a clear explanation of the different steps.

Part I incorporates the elements needed to bring about a partial separation of the hydrogen sulphide from the other constituents in the gas under analysis before the method is implemented. To this end, a sampling loop 1 in gold is provided which allows the condensible constituents in the gas to be trapped, the loop then being connected to a means such as a chromatographic separator, known to the skilled person, for separating the different constituents, so that only the hydrogen sulphide is retained. The gold loop 1 can be connected to a trap 2 with a variable temperature which will eliminate any residual water.

The separated hydrogen sulphide is then fed from the trap 2 across vacuum line 3 towards a quantification device such as a calibrated volume 4 connected to a pump of the TOEPLER type shown by reference 5 (part II of the drawing).

The vacuum line 3 is fitted with gauges J1 and J2 so that the gas transfer can be controlled. The control procedure is as follows: the gauge is initially at a pressure value Pi and since a gas transfer will cause an increase in pressure, the transfer is not stopped until the pressure reaches a value close to the initial pressure value Pi.

Part III incorporates the devices that will be used to prepare the sulphur and the hydrogen during the steps of the method. It contains a reactor 6 fitted with a valve 7, for example, an oven 8, a variable-temperature trap 9, auxiliary means 20 illustrated in FIG. 3C for introducing the oxidising agent, a device 21 (FIG. 3B) designed to bring the reactor to specified temperature conditions, in order to reach and maintain cryogenic conditions, for example.

The various devices are connected to the vacuum line 3 by pipes, valves and other means known to the skilled person.

Part IV consists of a storage receptacle 11 which can be connected to a device such as an IRMS for taking the isotopic measurement.

The valves and other control means, such as temperature and pressure sensors used to ensure that the steps of the method proceed smoothly, are not illustrated in this drawing since they are known and do not strictly constitute the essence of the invention.

The drawing-off or sampling loop 1 is preferably made from gold in order to provide better chemical inertia with respect to the hydrogen sulphide than would be possible if stainless steel were used, The reactors may be made from pyrex and will be fitted with valves such as those sold under the Kontès brand with glass plugs fitted with O-rings made from viton to guarantee a perfect seal during the transfer operations and for the connections to other elements such as the pump. They are designed for both types of reaction: oxidation of the $H_2S$ and reduction of the water.

The steps of the method are illustrated in FIG. 1B and FIGS. 3A to 3H. They are conducted on gases containing a small quantity of hydrogen sulphide, for example less than 50 $\mu$moles and preferably ranging between 5 and 50 $\mu$moles.

Preparatory Steps Prior to the Method

The quantity of hydrogen sulphide can be measured beforehand by chromatography using a method with which the skilled person will be familiar, then measured on the vacuum line using the calibrated volume before the oxidation step. This approach ensures chat the gas is transferred to the fullest extent possible, 90 to 95%, between the preparatory chromatographic step and the oxidation step.

The hydrogen sulphide separated in the gold sampling loop 1 is fed into the calibrated volume 4 via the pipe 3 so that its quantity can be accurately determined, FIG. 3A, this quantification step being conducted at a temperature close to ambient temperature whilst the transfer of gas to the calibrated volume is conducted under cryogenic conditions using liquid nitrogen to produce a temperature close to −196° C.

Steps of the Method
Step 1: Conditioning the Products by Oxidation
FIG. 3B

The separated and quantified hydrogen sulphide is transferred from the calibrated volume 4 into the oxidation reactor 6 via the vacuum line 3 in the. direction of the arrow and broken lines. The transfer step can be conducted under cryogenic conditions, the temperature of the reactor being approximately −196° C. in order to cause the hydrogen sulphide to condense thereby avoiding any leakage or loss of product and preventing any alteration of the gas.

The reactor 6 is disposed in an element 21 designed to produce and maintain cryogenic conditions.

A check is performed to ensure that all the hydrogen sulphide has been transferred, using one of the gauges arranged on the vacuum line, as mentioned above.

FIG. 3C

An oxidising agent such as excess oxygen is then introduced, The $H_2S$ remaining trapped by the liquid nitrogen, by means of a device 20 connected to the variable-temperature trap 2 and via section 22 of the vacuum line 3. The reactor 6 is still surrounded by the element 21.

FIG. 3D

The oxidation reactor is then closed and a step commenced during which the reactor is brought to a temperature at which the thermal conditions necessary for oxidation will be produced. To this end, the cryogenic element 21 is removed and the reactor 6 is placed inside the oven 8. The temperature to be reached is approximately 350° C. and this is maintained for a duration of 15 minutes. During this process, the hydrogen sulphide $H_2S$ is totally oxidised by virtue of the reaction $H_2S+3/2O_2-H_2O+SO_2$ and sulphur dioxide $SO_2$ water $HO_2$ are obtained, along with excess oxygen Which has not reacted.

The temperature of the reactor as well as the duration of the oxidation operation are selected so that the hydrogen sulphide will be completely oxidised. It would not be a departure from the scope of this invention if this step were performed using means other than an oven that would fulfil the same function; it would be conceivable to place the reactor in a device in which the requisite temperature could be attained by means of a heat-carrying fluid or any other means.

A piezo-resistive pressure sensor is an efficient means which may be used to control the pressure inside the reactor, which will be in the region of 10 to 15 kPa after the oxygen has been added, at which point the temperature will be close to −196° C. Under these conditions, the amount of oxygen required to produce oxidation will vary from 100 to 150 $\mu$moles.

At the end of the oxidation reaction, the reactor 6 is connected to the Toepler pump 5 to evacuate any oxygen which has not reacted. The reactor 6 may be placed in liquid nitrogen, at a temperature in the order of −196° C., which will allow the two products $SO_2$ and $H_2O$ present to be trapped in condensed form.

At the end of this step, the reactor 6 essentially contains the useful products trapped in the liquid nitrogen.

Step 2: Separating the Sulphur Dioxide and the Hydrogen
FIGS. 3E and 3F

The next step consists in separating $SO_2$ and $H_2O$. To this end, a variable-temperature trap 9 is used, the initial temperature Ti of which will be approximately −196° C. This temperature Ti is then raised until it reaches a value Ts sufficient to release only the sulphur dioxide, at a temperature close to −105° C.

Step 3: Preparing the Sulphur Dioxide for Isotopic Measurement

The sulphur dioxide is released and pumped by the Toepler pump 5 and stored at a point or in a receptacle 11 before the isotopic measurement is taken (FIG. 3F).

Step 4: Reducing the Water to Produce Hydrogen

FIG. 3G

Since the $SO_2$ has been totally removed from the variable-temperature trap 9, the temperature of the trap 9 is raised from the value Ts to a temperature The, which is close to 90° C., for example, in order to release the water. The freed water is fed to a reactor of exactly the same type as reactor 6, containing an agent for reducing the water, for example activated zinc. This reactor is brought to a temperature close to −196° C. with the means 21 in order to trap the released water.

FIG. 3H

The reactor containing the water and activated zinc is removed from means 21 and brought to a temperature close to 480° C. and is maintained at this temperature for a long enough period, for example 30 mn, to reduce all of the water. At the end of this operation, hydrogen is obtained and the liberated oxygen which oxidises the activated zinc.

The hydrogen is separated by pumping by means of the Toepler pump 5 then stored in a receptacle or ampoule with a view to taking its isotopic measurement. During the pumping operation, the device containing the reducing agent is maintained at cryogenic conditions in order to trap any impurities.

Steps 1 to 3 outlined above are specifically devised to handle compounds with a low hydrogen sulphide content, less than 50 μmoles, whereas steps 4 and 5 can be used for compounds which contain hydrogen sulphide, regardless of quantity, without departing from the scope of the invention.

EXAMPLE

The example given below provides a clearer illustration of the results and advantages of the method. Table 1 sets out the isotopic measurements obtained for the sulphur by the method of bubbling with cadmium in accordance with the prior art and table II the method of the invention. Table II also contains the measurements obtained for the hydrogen using the steps proposed by the method of the invention.

TABLE I method of the prior art
The quantity of hydrogen sulphide present in the tests, expressed in μmoles, is at least in excess of 1000 μmoles

| $SO_2$ | $\delta^{34}S$ |
|---|---|
| Test 1 | 5.4 |
| Test 1 | 6.9 |
| Test 2 | 6.2 |
| Test 3 | 7.1 |
| Test 4 | 7.5 |
| Test 5 | 7.2 |

The average value of the isotopic value for the sulphur is 6.7 +/− 0.8.

TABLE II

Method of the Invention
The gas used to test the method was $H_2S$, N27, marketed by Air Liquid, with a purity of 99.7% and a $CO_2$ content of less than 0.15%. The quantities of hydrogen sulphide in this gas vary between 5 and 50 μmoles.

| $H_2S$ in μmoles | $SO_2$ in μmoles | $\delta^{34}S$ | $H_2$ in μmoles | $\delta D$ |
|---|---|---|---|---|
| 9.5 | 9.5 | 7.1 | 11.7 | −183 |
| 21 | 20 | 6 | 23 | −193 |
| 22 | 20 | 7.1 | 23 | −196 |
| 26 | 25 | 6.3 | 26 | −193 |
| 34 | 36 | 6.2 | 32 | −186 |
| 34 | 32 | 6.1 | 34 | −185 |
| 53 | 54 | 5.8 | 53 | −172 |

The mean value of the isotopic measurement of the sulphur is 6.4 +/− 0.5.

The mean value of the isotopic measurement of the hydrogen is −187 +/− 8.

The recovery yield of the $SO_2$ and $H_2$ from the preparatory step to the measurement step is approximately 100%.

The isotopic measurement values set out in table II prove that the method of the invention can be applied with gases in which the hydrogen sulphide is present in a small quantity, for example from 5 to 50 μmoles, hence a quantity at least 200 times less than the quantity needed to produce the same results using the methods of the prior art.

As mentioned above at the beginning of this description, the isotopic measurements of the sulphur $\delta^{31}S$ can be used to characterise the genetic origin of the hydrogen sulphide whilst those for hydrogen $\delta D$ can be used as an indicator of the migration conditions of the hydrogen sulphide.

The curves given in FIGS. 4 and 5 were obtained using the maethod on three samples of organic sulphurous substances of different geographic origins G (Sicily), B (Venezuela) and M (USA).

The quantities of hydrogen sulphide contained in each sample are approximately 5 to 30 μmoles.

Figure 1B:
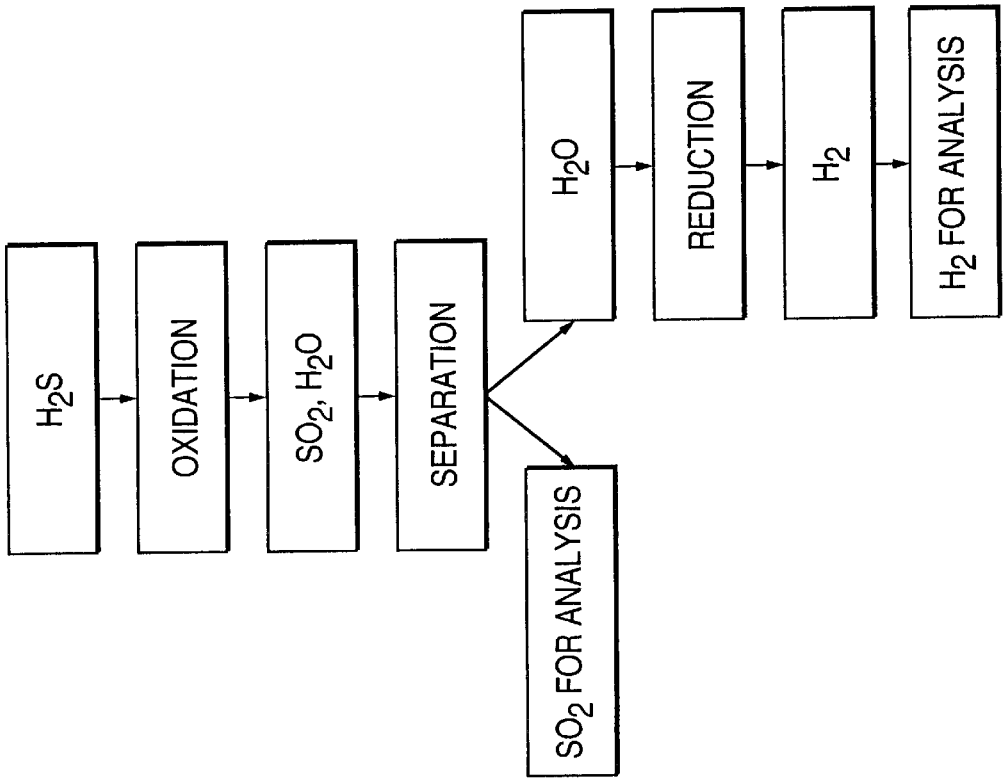
Figure 1A:
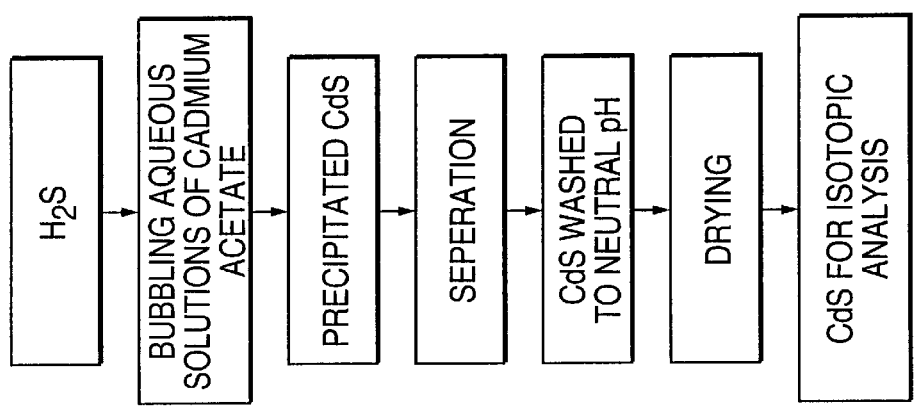
Figure 3A:
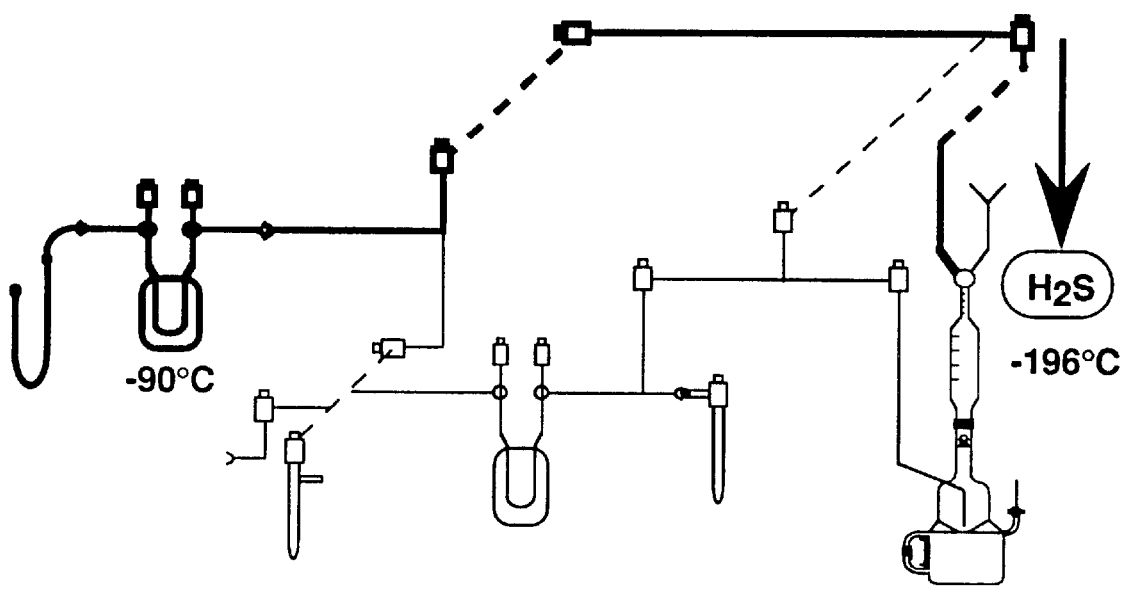
Figure 3B:
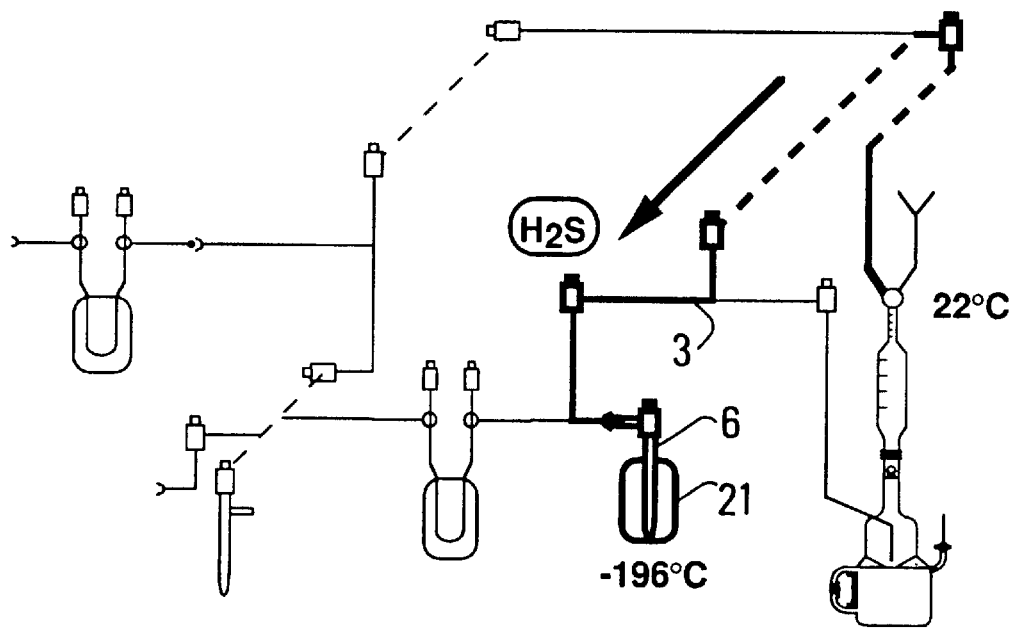
Figure 3C:
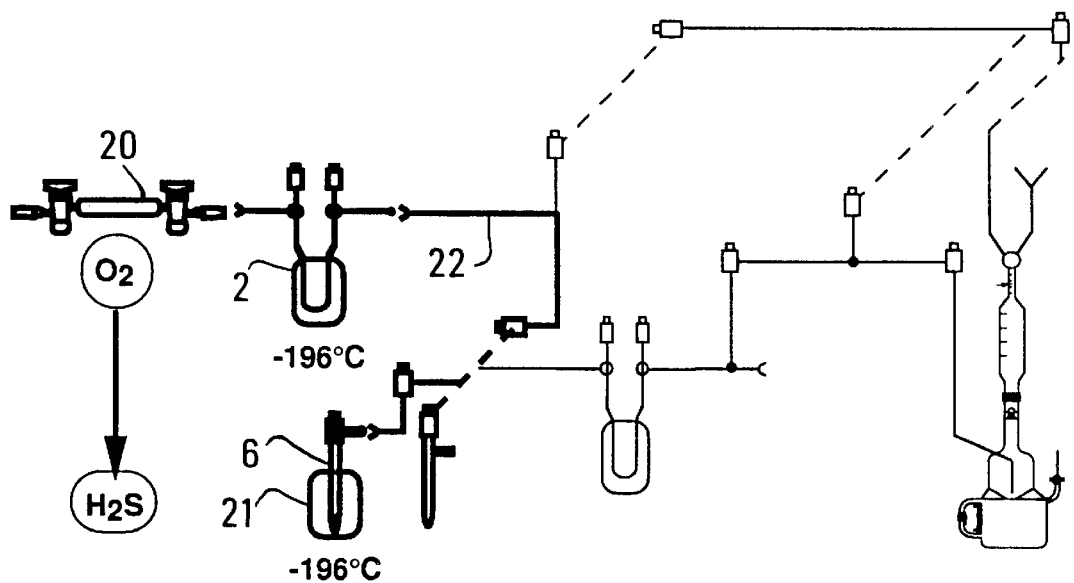
Figure 3D:
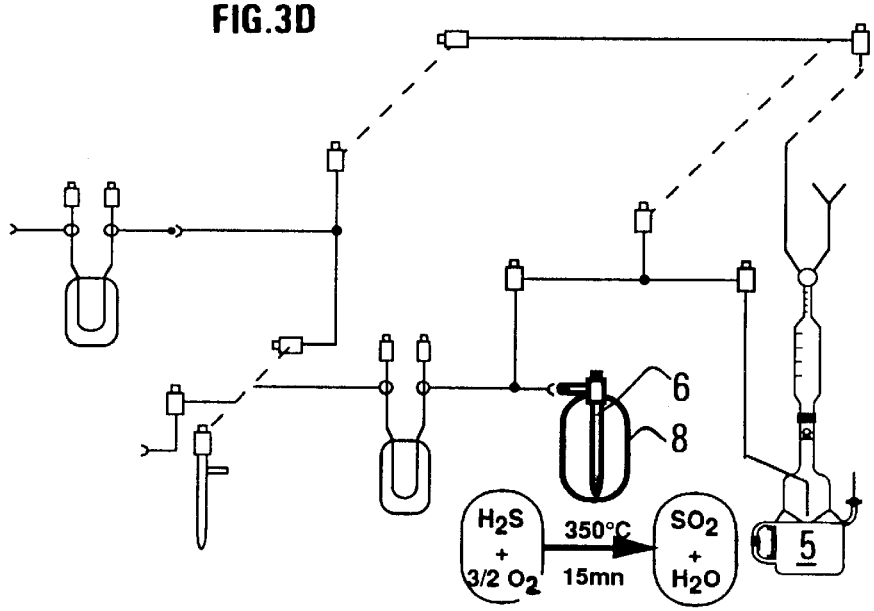
Figure 3E:
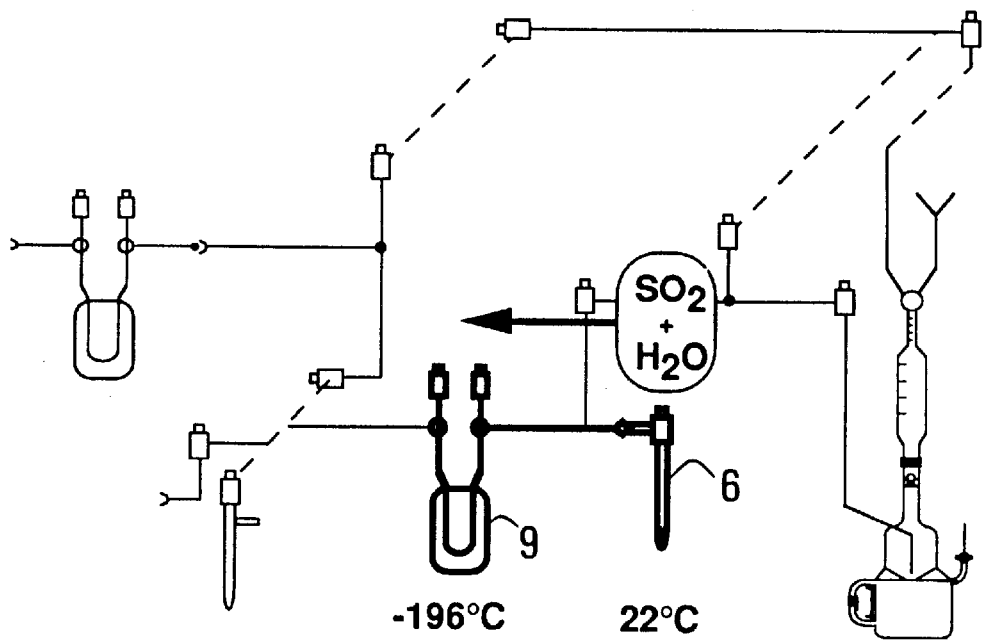
Figure 3F:
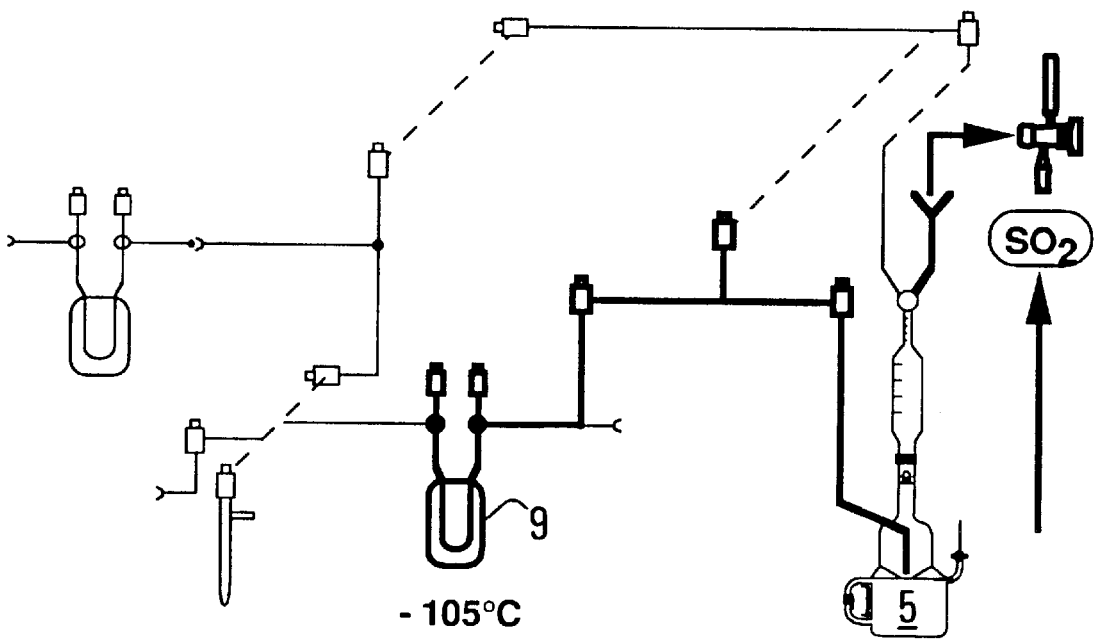
Figure 3G:
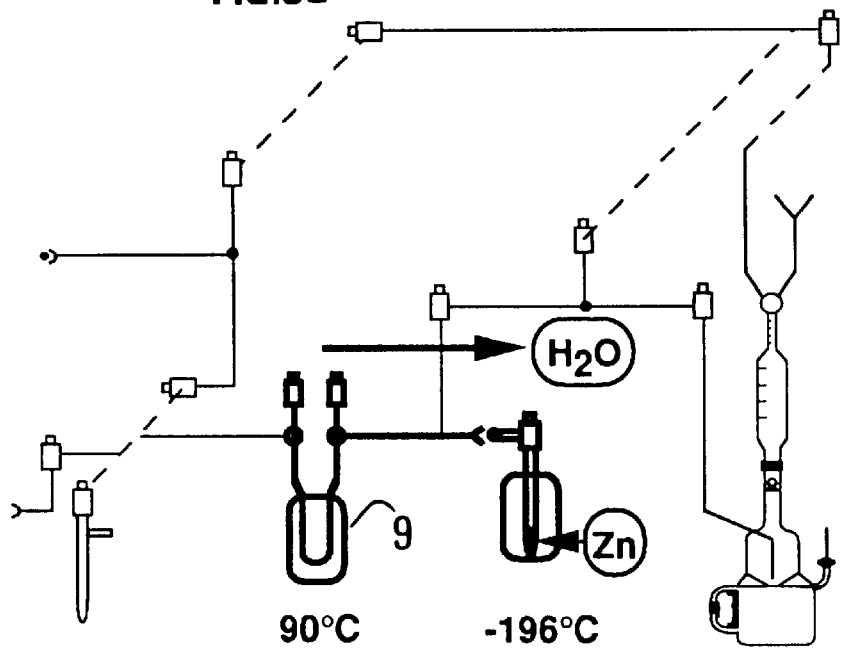
Figure 3H:
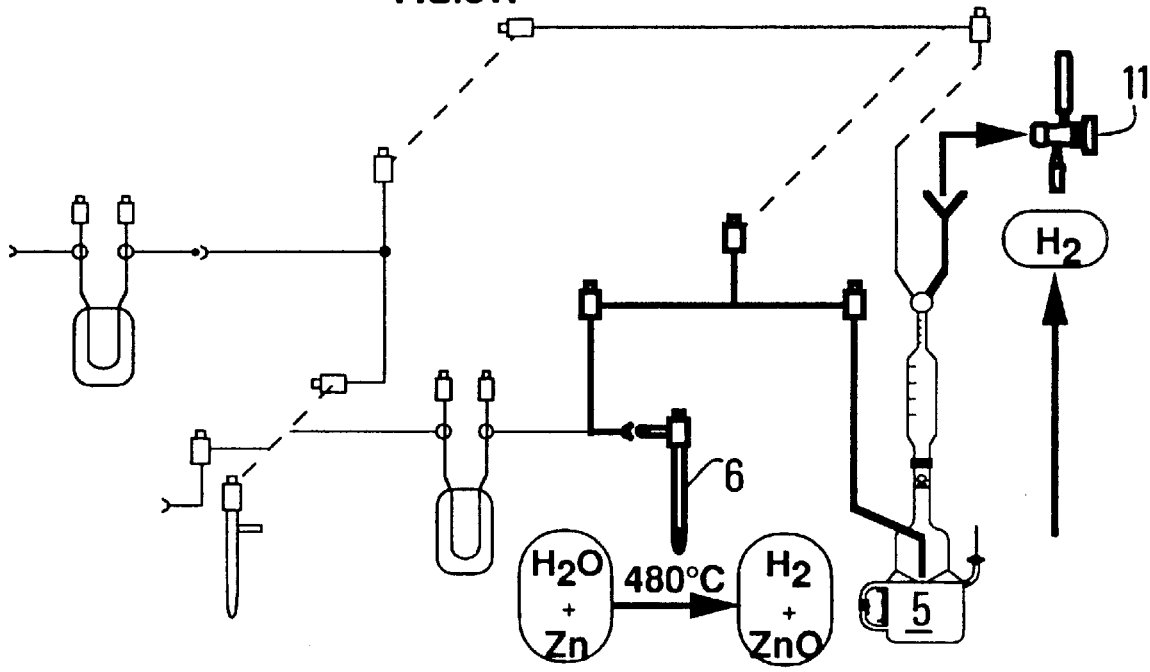
Figure 5:
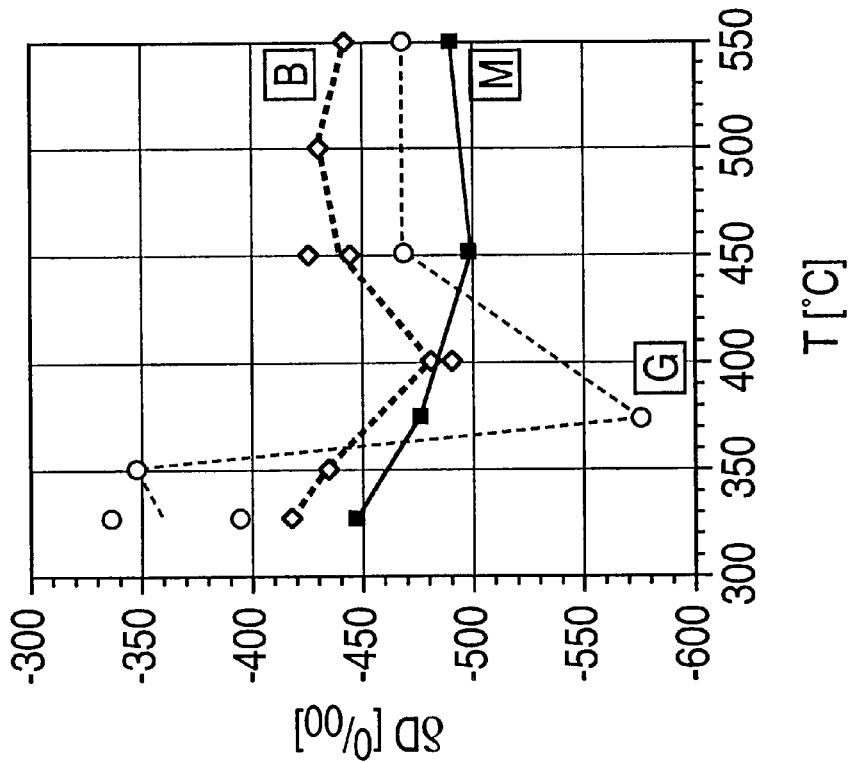
FIG. 5 shows, for the same samples, the results of the isotopic measurements on hydrogen in a temperature/isotopic value diagram.
Figure 4:
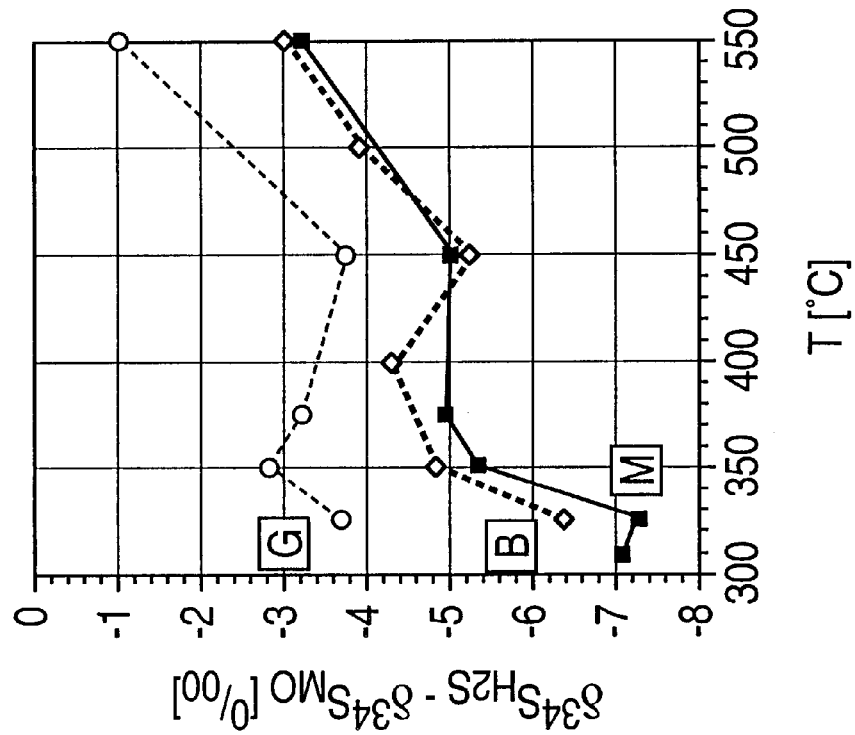
FIG. 4 shows the isotopic values obtained for the sulphur in a diagram of coordinates in which the abscissa corresponds to the temperature to which the organic sulphurous substance is heated and the ordinate corresponds to the isotopic measurements expressed as a relative value: relative isotopic measurement of the sulphur relative to the source value.

Without departing from the scope of the invention, the method of the invention can be applied as a means of preparing the sulphur and/or hydrogen contained in hydrogen sulphide in low quantities, in the field of environmental pollution for example;

in the case of hydrogen sulphide present in a small quantity in car exhaust gases, the method could be used to determine the origin of the sulphur, which may essentially be from the fuels and/or the lubricants, in the case of hydrogen sulphide contaminating underground gas stores, the method can be used to confirm whether or not the source of the sulphur is linked to microbial activity inherent in sulphate reduction.

What is claimed is:

1. A method enabling sulphur and hydrogen contained in hydrogen sulphide, $H_2S$, to be conditioned, said method consisting of the following steps;
   1) oxidizing the $H_2S$ at a temperature and for a period selected so as to produce total oxidation of the $H_2S$ into $SO_2$ and at least two products are obtained at the end of this step: $SO_2$ and $H_2O$,
   2) separating the two products obtained at the end of step 1), $SO_2$ and $H_2O$,
   3) obtaining an isotopic measurement on sulphur contained in the sulphur dioxide obtained at the end of step 2),
   4) bringing the $H_2O$ obtained from step 2) into contact with an agent capable of reducing the water to hydrogen form, and
   5) obtaining an isotopic measurement of the hydrogen.

2. A method as claimed in claim 1, wherein the products or elements, $SO_2$, $H_2$, $H_2S$, are transferred under conditions substantially close to cryogenic conditions.

3. A method as claimed in claim 1, wherein the step of separating the products $SO_2$ and $H_2O$ (step 2) is conducted at a temperature close to $-100°$ C. in order to release the sulphur dioxide and then at a temperature in the order of $90°$ C. to release the water.

4. A method as claimed in claim 1, wherein activated zinc is used as the agent for reducing the water in step 4.

5. A method as claimed in claim 2, wherein the hydrogen produced in step 4) is separated under cryogenic conditions in order to trap any impurities.

6. A method as claimed in claim 1, wherein at least steps 1) to 3) are conducted on a product containing a small quantity of hydrogen sulphide less than 50 $\mu$moles.

7. A method as claimed in claim 1, wherein the isotope of the sulphur and the hydrogen making up the hydrogen sulphide present in a natural gas is measured.

8. A method as claimed in claim 6, wherein at least steps 1) to 3) are conducted on a product containing a small quantity of hydrogen sulphide between 5 and 50 $\mu$moles.

9. A method of measuring hydrogen sulphide, $H_2S$, present in a geological formation by treating sulphur and hydrogen contained in said $H_2S$, said method consisting of:
   1) oxidizing the $H_2S$ from said geological formation at a temperature and for a period selected so as to produce total oxidation of the $H_2S$ into $SO_2$ and at least two products are obtained at the end of this step: $SO_2$ and $H_2O$,
   2) separating the two products obtained at the end of step 1), $SO_2$ and $H_2O$,
   3) obtaining an isotopic measurement of sulphur contained in the sulphur dioxide, $SO_2$, obtained at the end of step 2),
   4) bringing the $H_2O$ obtained from step 2) into contact with an agent capable of reducing the water to hydrogen form, and
   5) obtaining an isotopic measurement of said hydrogen.

* * * * *